United States Patent
Zhang et al.

[11] Patent Number: 5,991,044
[45] Date of Patent: Nov. 23, 1999

[54] METHOD AND APPARATUS FOR DETERMINING CHARACTERISTICS OF MICROSTRUCTURES UTILIZING MICRO-MODULATION REFLECTANCE SPECTROMETRY

[75] Inventors: Yaohui Zhang; Zhoa Siping; Li Ming Fu; Andrew Yen; George Sheng, all of Singapore, Singapore

[73] Assignee: Institute of Microelectronics, Singapore, Singapore

[21] Appl. No.: 08/869,058

[22] Filed: Jun. 4, 1997

[51] Int. Cl.[6] .................................................. G01N 21/25
[52] U.S. Cl. ......................... 356/417; 356/432; 356/445
[58] Field of Search ................................. 356/432, 432 T, 356/445

[56] References Cited

U.S. PATENT DOCUMENTS

| | | | |
|---|---|---|---|
| 4,720,191 | 1/1988 | Siegel et al. | 356/237 |
| 4,991,962 | 2/1991 | Jain | 356/349 |
| 5,159,412 | 10/1992 | Willenborg et al. | 356/445 |
| 5,220,403 | 6/1993 | Batchelder et al. | 356/432 |
| 5,270,797 | 12/1993 | Pollak et al. | 356/432 |

*Primary Examiner*—Frank G. Font
*Assistant Examiner*—Roy M. Punnoose
*Attorney, Agent, or Firm*—Proskauer Rose LLP

[57] ABSTRACT

A method and apparatus for measuring the characteristics of microstructures by modulating a sample using a modulated source and utilizing a microscope to magnify a desired sample area and direct a monochromatic probe light source onto the desired microstructure of the sample. The probe light is reflected by the sample and the reflectance spectra is directed by the microscope and thereafter, is detected and transmitted to a computer to record or display the measured characteristic. Further, the computer is also used to control the brightness of the monochromatic probe light and to control the modulation frequency of the modulated source. The wavelength of the monochromatic probe light can also be varied by the computer. The magnification of the microscope can be varied so that the desired microstructure is visible and the probing light spot is precisely placed on it. The desired sample microstructure can be precisely located within the viewing field of the microscope through the use of an indicator like a cross line indicator.

19 Claims, 3 Drawing Sheets

METHOD AND APPARATUS FOR DETERMINING CHARACTERISTICS OF MICROSTRUCTURES UTILIZING MICRO-MODULATION REFLECTANCE SPECTROMETRY

FIELD OF THE INVENTION

This invention relates to a method and apparatus for accurately characterizing the physical parameters of microscopically small-size semiconductor materials and other microstructures by using micro-reflectance spectrometry.

BACKGROUND OF THE INVENTION

In the study of bulk semiconductor materials and low-dimensional semiconductor materials, it is very desirable to be able to accurately measure physical characteristics such as energy levels, critical points, electric-field distribution dopant concentration, etc. These characteristics may be measured using reflectance spectrometry which is a contactless and nondestructive measuring system that can operate at room temperature. The measurement of these characteristics is important for evaluating the quality and homogeneity of semiconductor materials.

The use of modulation reflectance spectrometry as a measuring system is known and is discussed at length in U.S. Pat. Nos. 5,287,169; 5,260,772; 5,255,071; 5,255,070; and 5,159,410, all to Pollak. The contents of those patents are incorporated herein by reference.

The technique of modulation reflectance spectrometry measures the effect that a periodically modulated source has on the reflectance spectra of a given sample, instead of directly measuring a given characteristic of the sample.

For instance, photoreflectance (PR) spectrometry uses a modulated light source. Electroreflectance (ER) spectrometry uses a modulated electric field. Other modulation methods can be used such as piezomodulation, thermal modulation, wavelength modulation, etc.

In the case of PR, a modulated light source and a monochromatic light source are directed at a sample through the use of lenses or mirrors. The modulated light source affects various parts of the sample differently depending on specific transitions in the sample composition and structure. The reflectance spectra of the sample is determined by the reflectance of the monochromatic light. The reflected light is received by a detector such as a photodiode, photoconductor, etc. The detector produces signals that are used to measure the desired characteristic and to adjust a variable neutral density filter. The neutral density filter regulates the intensity of the monochromatic light source for normalization.

In the case of ER, the sample is placed in a condenser-like system comprised of a pair of electrodes that produce a modulated electric field in response to an electromodulation source. As with the above noted PR system, a monochromatic light source is directed at the sample and the reflected light is received by a detector which produces signals that are used to measure the desired sample characteristic and to normalize the monochromatic light source.

The problem in the past has been that these systems could only operate on sample sizes with an area of more than 1.0 $mm^2$. This was due to a limitation in the prior art reflectance systems which could not collect the reflected light of a focused optical spot that was smaller than 1.0 $mm^2$. This corresponds to an area which is considerably larger than the discrete segments (e.g., gate junctions) that comprise semiconductor devices and prevents the prior art reflectance systems from being used to characterize small-size semiconductor devices and microstructures. This characterization is very important in the analysis of semiconductor materials.

Oftentimes, the purpose of analyzing semiconductor materials is to ascertain the qualities of the various sample areas. These qualities are determined by the various conditions under which a given semiconductor material is grown. Imperfections in the semiconductor material are indicative of improper growth conditions (e.g., temperature, vacuum, growth material, etc.) and to correct these imperfections it is necessary to be able to isolate specifically what step in the process of fabrication caused the imperfections. To do this, one must be able to measure specific microstructures within the semiconductor material.

A further problem with the prior art reflectance system is that it is very difficult to set up the monochromatic light source and the detector to measure the characteristics of a specific desired portion of the sample such as a specific gate junction.

Therefore, it is an object of the present invention to utilize a method of micro-reflectance spectrometry that is capable of measuring sample sizes and sample areas smaller than 1.0 $mm^2$.

Another object of this invention is to provide an improved apparatus that utilizes micro-reflectance spectrometry to characterize sample sizes smaller than 1.0 $mm^2$.

A further object of this invention is to provide a method of directing a probing light spot through the use of a microscope capable of achieving a spatial resolution of less than 1.0 $\mu m$ utilizing micro-reflectance spectrometry.

A still further object of this invention is to provide an improved apparatus that utilizes micro-reflectance spectrometry and is capable of achieving a spatial resolution of less than 1.0 $\mu m$.

SUMMARY OF THE INVENTION

These and other objects of the present invention are achieved by utilizing a lens of an optical microscope to direct a monochromatic probe light and to magnify microstructures of a sample that are of interest. A modulated source (e.g., photomodulated, electromodulated, piezomodulated, thermal modulated, wavelength modulated, etc.) is also directed at the sample and the effect of the modulated source on the sample may be determined by detecting the reflection spectra of the sample. The reflection spectra of the sample may be analyzed by a computer to characterize the sample and to normalize the operating conditions of the system by adjusting the brightness of the probe monochromatic light through the use of a variable neutral density filter. The computer can also utilize step motors that adjust the wavelength of the monochromatic light and the modulation frequency of the modulated source to optimize the conditions for a given measurement.

In operation, micro-reflectance spectrometry as practiced according to the present invention, can achieve spatial resolutions of less than 1.0 $\mu m$. This is preferably accomplished by adjusting the magnification of the microscope to direct the monochromatic light and produce a probing light spot on an area of interest. An illuminating lens of the microscope is used to direct the probing light spot while a viewing lens of the microscope is used to locate the area of interest. Once the probing light spot is correctly directed, a detector is placed before the viewing lens to measure the reflectance spectra of the sample.

As a result, the prior art limitation on a minimum sample size of 1.0 $mm^2$ can be reduced to areas smaller than 1.0 $\mu m^2$ by the present invention, therein enabling convenient measurement of microstructures that are of interest.

BRIEF DESCRIPTION OF THE DRAWINGS

Following is a description of an embodiment, which when taken in connection with the following drawings, will illustrate the above noted features and advantages as well as further ones. It should be expressly understood that the drawings are included for illustrative purposes and do not represent the metes and bounds of the invention.

DETAILED DESCRIPTION OF THE PREFERRED EMBODIMENTS

Figure 1:
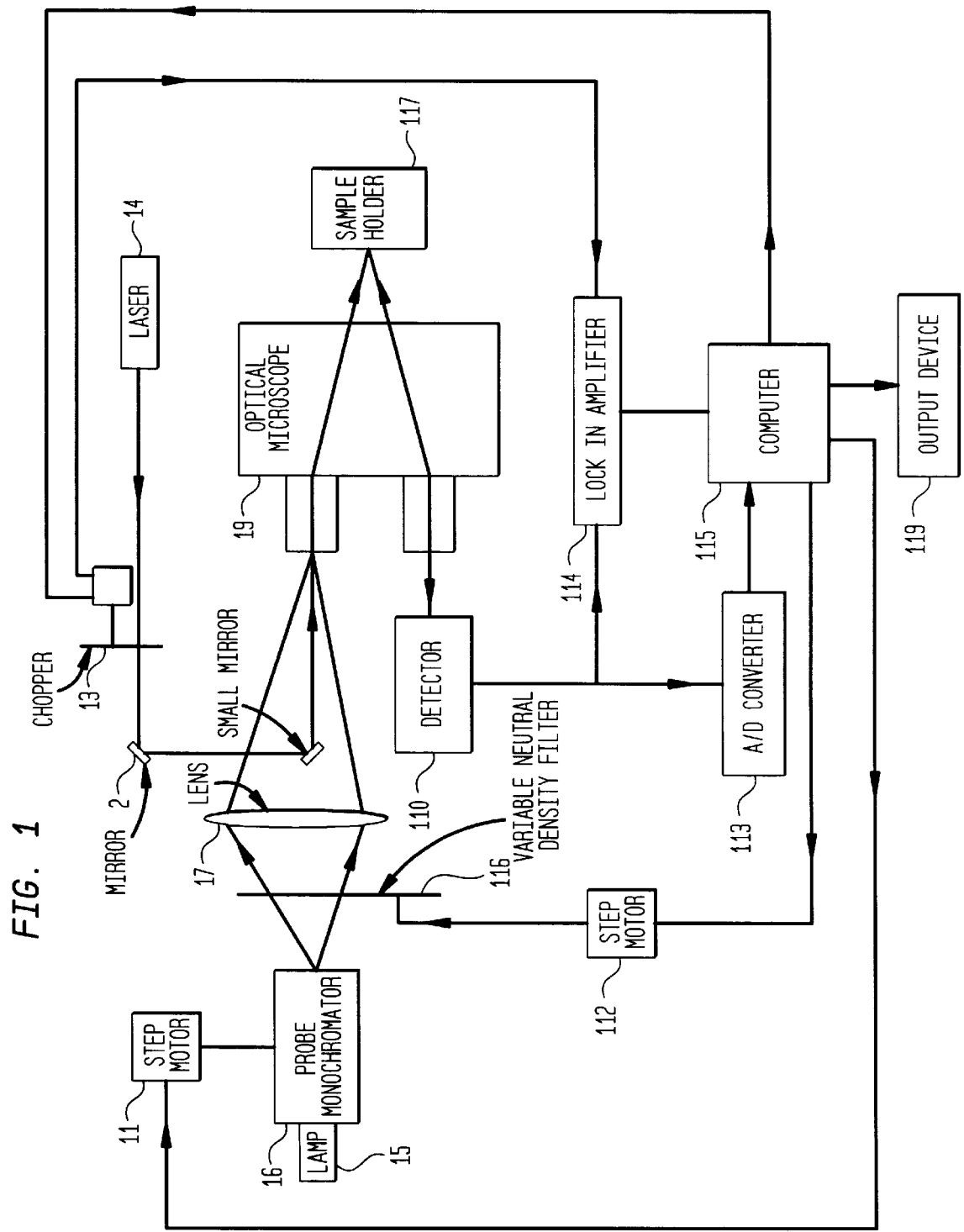
FIG. 1 is a schematic block diagram of an apparatus for a photo-reflectance system in accordance with a preferred embodiment of the present invention.

In the drawings, like references numerals are used to designate like parts. In terms of the present invention, a modulated source can be photomodulated, electromodulated, piezomodulated, thermal modulated, wavelength modulated, etc. The invention is described with reference to a preferred embodiment using a photomodulated source and an electromodulated source but many other modulated sources such as piezomodulated, thermal modulated, wavelength modulated, etc., can be used without departing from the spirit and scope of the subject invention.

Micro-Photoreflectance Spectrometer

As seen in FIG. 1, a micro-reflectance device according to a preferred embodiment of the present invention is provided by a novel combination of a photoreflectance device and an optical microscope. As a result of this combination, the spatial resolution of the PR device is drastically improved by a factor of 100,000 per cent or more.

Specifically, as shown in FIG. 1, a light source 15 produces light which passes through a probe monochromator 16 that is driven by a step-motor 11 to produce a monochromatic probing light source of a given wavelength. A variable neutral density filter 116 controls the intensity of the monochromatic probing light which is then focused by a lens 17 through an illuminating lens of an optical microscope 19. The microscope 19 directs a probing light spot onto a sample (not shown) that is held by a sample holder 117.

The microscope 19 is used to precisely direct the probing light source onto the sample and to direct the reflectance signal from the sample to a detector. The magnification of the microscope can be adjusted precisely to focus the probing light spot onto a desired microstructure and through the use of different levels of magnification, the focus spot can be greatly reduced from the prior art reflectance spectrometers enabling characterization of microstructures that prior spectrometers could not characterize.

In operation, the probing light spot can be precisely directed to the sample to achieve a spatial resolution of less than 1.0 $\mu$m by adjusting the magnification of the microscope 19 such that the desired area of the sample is visible and illuminated by the probing light spot. Positioning of the sample within the optical field is accomplished by viewing the sample through a viewing lens of the microscope 19. The positioning can be further facilitated by use of a microscope that has a cross line or other focal point indicating apparatus viewable within the focusing field.

The magnification of the microscope 19 can be adjusted to direct the probing light spot at a specific microstructure (e.g., gate junction) of interest. Once the sample is properly positioned and the magnification is properly set to direct the probing light spot, a detector 110 is placed before the viewing lens of the microscope.

Photoexcitation of the sample is maintained by a laser 14 which produces a beam that is modulated by a chopper 13 and then directed to the sample through the illuminating lens of the microscope 19 by a mirror 12 and a small mirror 18.

The probing light spot produces a reflectance spectra of the sample which contains both an a.c. and a d.c. component and is received by the detector 110. A filter 111 is positioned between the detector 110 and the viewing lens of the microscope 19 to filter out light that is reflected from the modulated light source. The detector 110 produces both an a.c. signal and a d.c. signal in response to receipt of the reflectance spectra of the sample. The a.c. signal from the detector 110 is supplied to a lock-in amplifier 114 which also receives a signal from the chopper 13 that is related to the modulation frequency of the laser 14. The lock-in amplifier 114 produces an output signal related to the modulation frequency and the photoreflectance signal and provides that output signal to a computer 115. The computer 115 also receives the d.c. signal from the detector 110 through an A/D converter 113 which converts the d.c. signal into a digital representative thereof.

The computer 115 produces a signal that represents the measured characteristic. The signal from the output of the computer 115 is provided to an output device 119. As used herein, the term output device is intended to encompass any device such as a display monitor, printer, plotter, digital recorder, etc. that reproduces, displays, records, or otherwise creates a representation of the measured characteristic for easy reference.

Additionally, the computer 115 acts as a controller that controls a step motor 11, a step motor 112 and the chopper 13 through the use of three separate control signals in the conventional manner. The computer 115 (acting as controller, as further discussed below) produces a signal which is received by the step motor 11 and controls the wavelength of the probing light source from the probe monochromator 16 for a given measurement. The computer 115 also produces a signal that is received by the step motor 112 which controls a variable neutral density filter 116 to maintain the d.c. component of the reflectance spectra received by the detector 110 constant for normalization. Lastly, the computer 115 controls the modulation frequency of the chopper 13.

Micro-Electroreflectance Spectrometer

Figure 2:
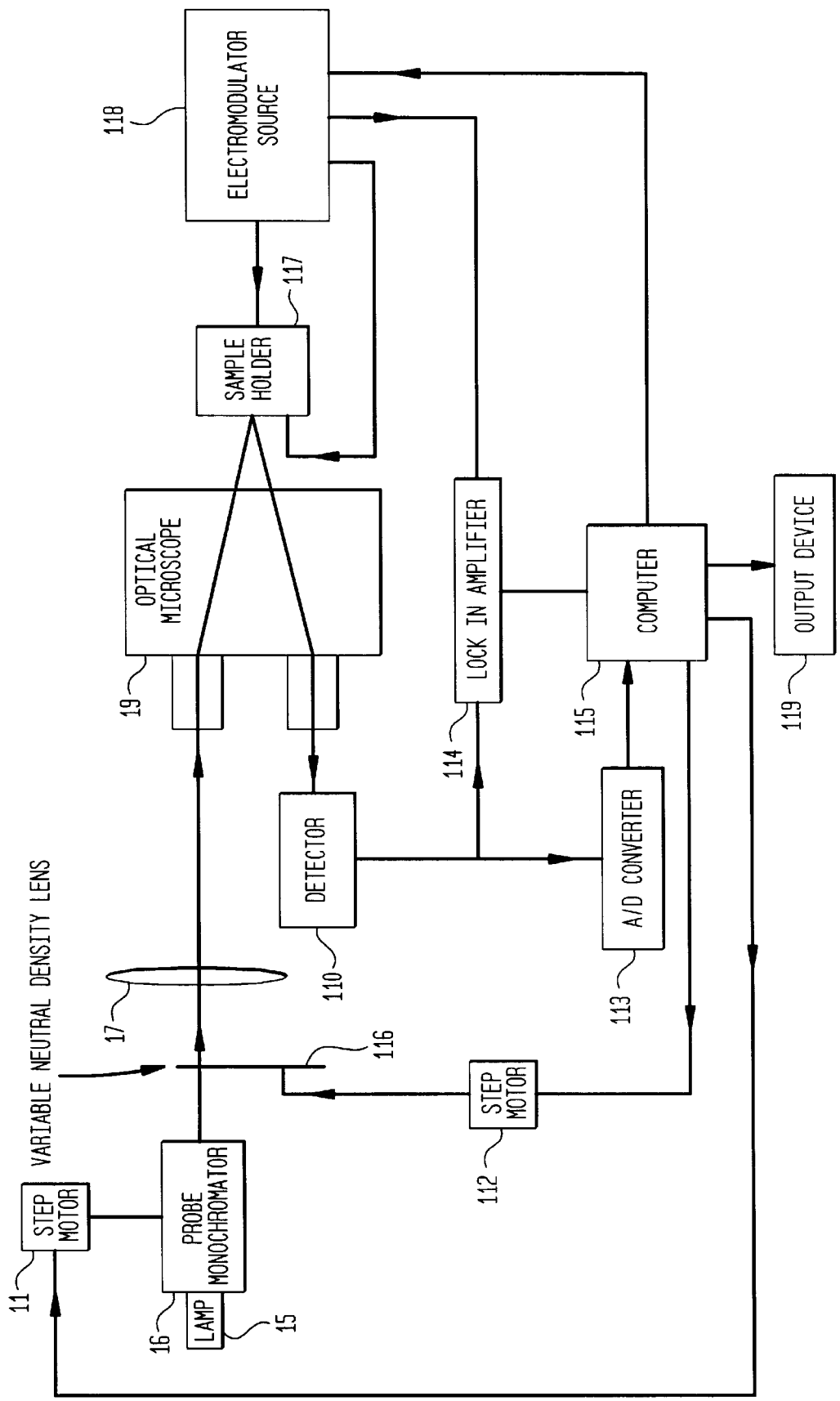
FIG. 2 is a schematic block diagram of an apparatus for an electroreflectance system in accordance with a preferred embodiment of the present invention.
Figure 3:
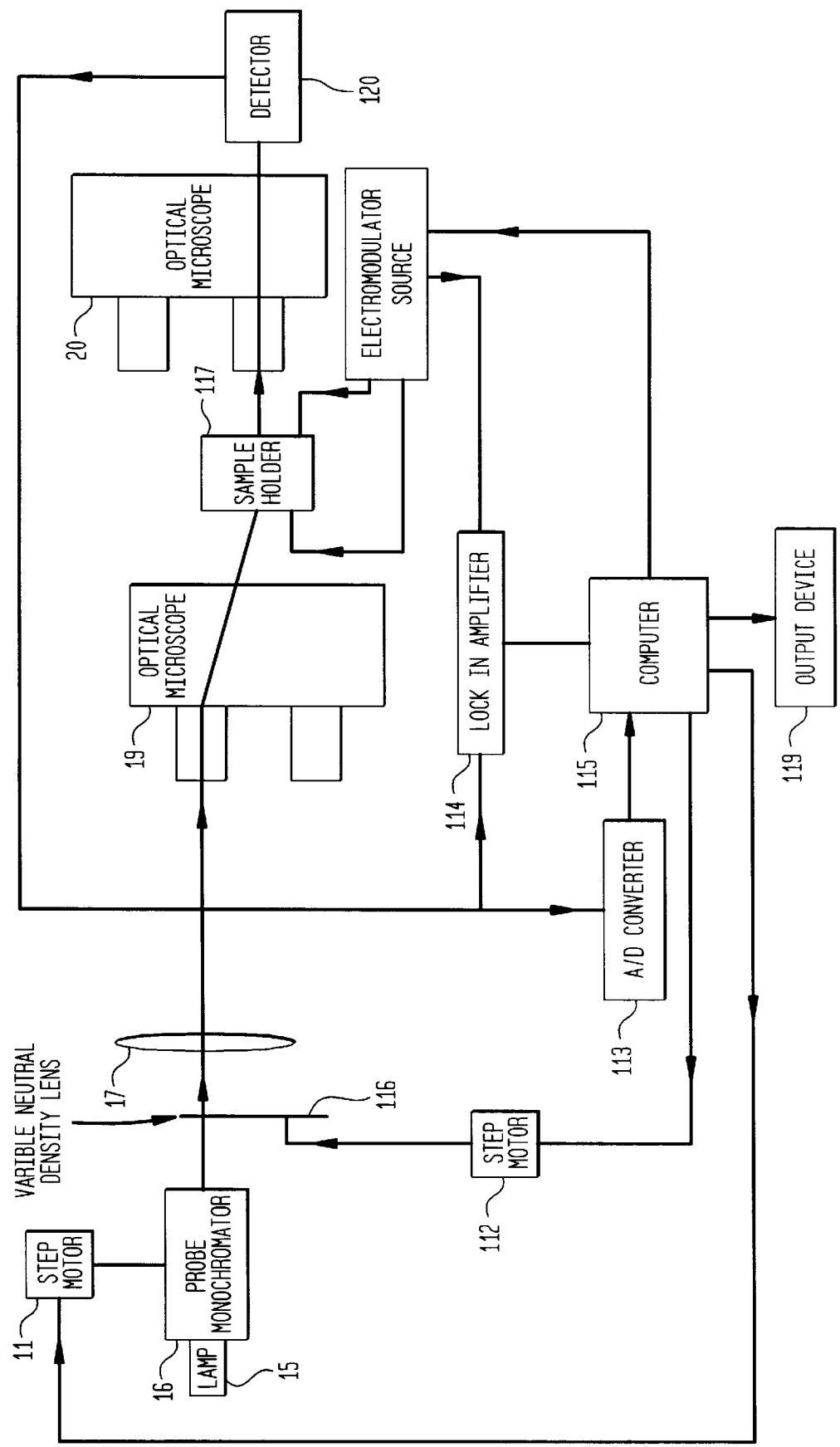
FIG. 3 is a schematic block diagram of an apparatus for an electrotransmittance system in accordance with a preferred embodiment of the present invention.

The micro-electroreflectance spectrometer shown in FIG. 2 operates similar to the micro-photoreflectance spectrometer shown in FIG. 1 and like parts have the same function as described above. The distinction is that in micro-electroreflectance spectroscopy, the sample of interest is excited through the use of a modulated source, such as a electromodulator, a piezomodulator, a photomodulator and a thermal modulator. Illustratively, an electromodulator source 118 is shown in FIGS. 2 and 3; however, it should be understood that source 118 may be substituted by any of the above-mentioned modulators. Electromodulation source 118 is connected to conductive plates (not shown) placed on either side of the sample. The modulation frequency of the electromodulation source 118 is controlled by the output of a computer 115 (which acts as a controller, as further discussed below) in the same way as the modulation of the laser 14 is controlled in the micro-photoreflectance spectrometer described above.

As with micro-photoreflectance, a probe monochromator 16 is directed by a lens 17 through an illuminating lens of a microscope 19 to produce a probing light spot on a sample (not shown) that is held by a sample holder 117. The reflectance spectra which contains both an a.c. and a d.c. component is detected by a detector 110 after proper positioning of the probing light spot. In response to the reflectance spectra, the detector 110 produces both an a.c. signal that is received by a lock-in amplifier 114 and a d.c. signal that is converted to a digital equivalent by an A/D converter 113 and is thereafter received by the computer 115.

The electromodulation source 118 produces a signal that is related to its modulation frequency which is received by the lock-in amplifier 114. In response to the received signal from the electromodulation source 118 and the a.c. signal from the detector 110, the lock-in amplifier 114 transmits a signal to the computer 115 which in response thereto, produces a signal that represents the measured characteristic. The signal from the output of the computer 115 is provided to an output device 119.

The computer 115 also acts as a controller that controls the wavelength and the intensity of the monochromatic probing light source through the use of step motors 11 and 112, as described above.

In micro-electroreflectance, there is no need for a filter to be placed between the detector 110 and the viewing lens of the microscope 9 since there is no reflectance caused by the electromodulator source 118.

While the preferred embodiments have been described with reference to reflectance spectrometry, a simple modification can be made for micro-transmittance spectrometry.

Micro-Electrotransmittance Spectrometer

In FIG. 3 is shown an example of a micro-electrotransmittance spectrometer in accordance with the present invention. The micro-electrotransmittance spectrometer operates similar to the micro-electroreflectance spectrometer described above with the exception that a second optical microscope 20 is placed behind a sample that is being measured. The sample holder 117 must be constructed of a transparent material that does not block the transmittance spectra of the sample. The optical microscope 20 is focused on the microstructure of interest and a detector 120 is then placed behind a viewing lens of the optical microscope 20. The detector 120 detects the transmittance spectra through the microscope 20 and transmits a signal to the rest of the micro-transmittance system. This transmittance signal operates similar to the reflectance signals described above for micro-photoreflectance and micro-electroreflectance spectrometry. Therefore, the use herein of the term reflectance is intended to be broadly interpreted to encompass both reflectance and transmittance and the term reflectance spectrometry is intended to also encompass transmittance spectrometry.

Conclusion

By using the methods and apparatus of: the presently disclosed invention, the characteristics of sample sizes smaller than $1.0 \mu m^2$ can be analyzed and a spatial resolution of less than $1.0 \mu m$ can be achieved. This represents 100,000 per cent improvement over the prior art reflectance spectrometry systems.

While the invention has been described with reference to the preferred embodiments, it will be apparent to those skilled in the art that numerous variations can be made without departing from the spirit or scope of the invention which is defined by the appended claims. The preferred embodiments were described above solely for illustrative purposes and were not intended to limit the metes and bounds of the appended claims.

We claim:

1. A method of measuring characteristics of microstructures, the method comprising the steps of:

a. directing a monochromatic non-infrared light source, having a wavelength less than $0.7 \mu m$, through a lens of a microscope onto a desired microstructure of a sample to achieve a spatial resolution of less than $1.0 \mu m$;

b. exciting the sample by a modulated source;

c. detecting the reflectance of the monochromatic light source.

2. The method of claim 1, wherein the step of exciting the sample further comprises using a photomodulation source to excite the sample.

3. The method of claim 1, wherein the step of exciting the is sample further comprises using an electromodulation source to excite the sample.

4. The method of claim 1, wherein the step of exciting the sample further comprises using a piezomodulation source to excite the sample.

5. The method of claim 1, wherein the step of exciting the sample further comprises using a thermal modulation source to excite the sample.

6. The method of claim 1, wherein the step of exciting the sample further comprises using a wavelength modulation source to excite the sample.

7. The method of claim 1, further comprising after the step of detecting the reflectance of the monochromatic light source, producing a stable measuring system.

8. The method of claim 1, further comprising after the step of detecting the reflectance of the monochromatic light source, producing a signal representative thereof and providing the representative signal to an output device.

9. The method of claim 1, further comprising after the step of detecting the reflectance of the monochromatic light source, producing a signal representative thereof and providing the representative signal to a controller device for controlling said measuring method.

10. The method of claim 1, wherein the step of directing a monochromatic light source through the lens of the microscope further comprises directing the monochromatic light source using a focal point indicator.

11. An apparatus for measuring the characteristics of microstructures comprising:

a. a source of monochromatic non-infrared light having a wavelength less than $0.7 \mu m$;

b. a microscope configured to direct the monochromatic light onto a sample to achieve a spatial resolution of less than 1.0 μm, and to transmit a reflectance signal therefrom;

c. a modulator to excite the sample; and d. a detector for detecting the reflectance signal and producing a signal representative thereof.

12. The apparatus of claim 11, wherein the modulator is a photomodulator.

13. The apparatus of claim 11, wherein the modulator is an electromodulator.

14. The apparatus of claim 11, wherein the modulator is a piezomodulator.

15. The apparatus of claim 11, wherein the modulator is a thermal modulator.

16. The apparatus of claim 11, wherein the modulator is a wavelength modulator.

17. The apparatus of claim 11, further comprising an output device which receives said signal from said detector.

18. The apparatus of claim 11, further comprising a controller that receives said signal from said detector for controlling said apparatus.

19. The apparatus of claim 11, wherein the microscope further comprises a focal point indicating apparatus.

* * * * *

UNITED STATES PATENT AND TRADEMARK OFFICE
CERTIFICATE OF CORRECTION

PATENT NO : 5,991,044
DATED : November 23, 1999
INVENTOR(S): Yaohui Zhang, et al.

It is certified that error appears in the above-identified patent and that said Letters Patent is hereby corrected as shown below:

The title page, item 75, the second inventor's name should read:
   Zhao Siping

Signed and Sealed this

Twelfth Day of December, 2000

*Attest:*

Q. TODD DICKINSON

*Attesting Officer*   *Director of Patents and Trademarks*